US012456546B2

(12) United States Patent
Wu et al.

(10) Patent No.: US 12,456,546 B2
(45) Date of Patent: Oct. 28, 2025

(54) CLOUD-BASED HEARING AID MANAGEMENT SYSTEM AND METHOD THEREOF

(71) Applicant: DIGIBIONIC LIFESTYLE CO., LTD., New Taipei (TW)

(72) Inventors: Chih-Hsien Wu, New Taipei (TW); Yu-Hsun Lin, New Taipei (TW); Fu Jie Tey, New Taipei (TW)

(73) Assignee: DIGIBIONIC LIFESTYLE CO., LTD., New Taipei (TW)

( * ) Notice: Subject to any disclaimer, the term of this patent is extended or adjusted under 35 U.S.C. 154(b) by 265 days.

(21) Appl. No.: 18/137,464

(22) Filed: Apr. 21, 2023

(65) Prior Publication Data

US 2024/0296931 A1 Sep. 5, 2024

(30) Foreign Application Priority Data

Mar. 2, 2023 (TW) ................................ 112107500

(51) Int. Cl.
*G16H 20/30* (2018.01)
*G16H 10/60* (2018.01)
*G16H 40/67* (2018.01)

(52) U.S. Cl.
CPC ............. *G16H 20/30* (2018.01); *G16H 10/60* (2018.01); *G16H 40/67* (2018.01)

(58) Field of Classification Search
CPC ......... G16H 20/30; G16H 10/60; G16H 40/67
See application file for complete search history.

(56) References Cited

U.S. PATENT DOCUMENTS 10,943,407 B1 * 3/2021 Morgan ................. G16H 15/00
2010/0172524 A1 * 7/2010 Durant .................. H04R 25/70
381/314

(Continued)

FOREIGN PATENT DOCUMENTS

CN 110225443 A 9/2019
CN 112954570 A 6/2021

OTHER PUBLICATIONS

S. Rajkumar, S. Muttan and B. Pillai, "Adaptive expert system for audiologists," 2011 International Conference on Communications and Signal Processing, Kerala, India, 2011, pp. 305-309, doi: 10.1109/ICCSP.2011.5739325. (Year: 2011).*

(Continued)

*Primary Examiner* — Sun M Li
(74) *Attorney, Agent, or Firm* — Birch, Stewart, Kolasch & Birch, LLP

(57) ABSTRACT

A cloud-based hearing aid management system and a method thereof is provided. The system includes a user device configured to output audiometry information and generate an audiogram based on a user's input indicating that if the audiometry information can be heard. The user device transmits the audiogram to a management server, such that the audiogram is converted into a hearing parameter, and hearing-loss characteristic value are extracted from the audiogram. The management server incorporates the hearing-loss characteristic value into a hearing aid recommendation table to generate corresponding hearing aid recommendation information. The present invention can recommend a hearing aid suitable for the user by operating a remote computer. In addition, the fitting staff adjusts the sound producing parameters of the hearing aid according to the user's requirement, which provides a convenient new consumption method.

8 Claims, 8 Drawing Sheets

(56) References Cited

U.S. PATENT DOCUMENTS

| | | | | |
|---|---|---|---|---|
| 2013/0343583 | A1* | 12/2013 | Marcoux | G16H 20/30 381/314 |
| 2014/0193008 | A1* | 7/2014 | Zukic | H04R 25/70 381/314 |
| 2014/0205117 | A1* | 7/2014 | Hou | H04R 25/70 381/312 |
| 2018/0103876 | A1* | 4/2018 | Davis | G16H 80/00 |
| 2020/0382884 | A1* | 12/2020 | Chang | A61H 39/00 |
| 2021/0329393 | A1* | 10/2021 | Swetlitz | A61B 5/7475 |

OTHER PUBLICATIONS

F. Chen, S. Wang, J. Li, H. Tan, W. Jia and Z. Wang, "Smartphone-Based Hearing Self-Assessment System Using Hearing Aids With Fast Audiometry Method," in IEEE Transactions on Biomedical Circuits and Systems, vol. 13, No. 1, pp. 170-179, Feb. 2019, doi: 10.1109/TBCAS.2018.2878341. (Year: 2019).*

Keidser G, Dillon H, Flax M, Ching T, Brewer S. The NAL-NL2 Prescription Procedure. Audiol Res. Mar. 23, 2011;1(1):e24. doi: 10.4081/audiores.2011.e24. PMID: 26557309; PMCID: PMC4627149. (Year: 2011).*

S. Akbarzadeh, E. Lobarinas and N. Kehtarnavaz, "Online Personalization of Compression in Hearing Aids via Maximum Likelihood Inverse Reinforcement Learning," in IEEE Access, vol. 10, pp. 58537-58546, 2022, doi: 10.1109/ACCESS.2022.3178594. (Year: 2022).*

F. Softie, R. Stojanović, Ž. Blagojević, Z. Bundalo and D. Pašalić, "Implementation of audiological measurements and correction of hearing damages using web technologies," 2015 4th Mediterranean Conference on Embedded Computing (MECO), Budva, Montenegro, 2015, pp. 383-386, (Year: 2015).*

* cited by examiner

CLOUD-BASED HEARING AID MANAGEMENT SYSTEM AND METHOD THEREOF

This application claims priority for TW patent application Ser. No. 112107500 filed on 2 Mar. 2023, the content of which is incorporated by reference in its entirely.

BACKGROUND OF THE INVENTION

Field of the Invention

The present invention relates to electrical communication technology, particularly to a cloud-based hearing aid management system and a method thereof.

Description of the Related Art

The development of hearing aid-related products is very important technology for the hearing-impaired people. Most hearing-impaired people can be helped to recover their hearing as long as they wear hearing aids.

Most of the sales methods of hearing aids today are traditional marketing methods, such as physical stores set up in general streets, or the physical sales stores of hearing aids set up in medical hospitals. However, the costs of renting physical stores and manpower therein are high, and these costs are correspondingly reflected in the price of hearing aids, which results in high prices for hearing aids. Due to economic conditions, many hearing-impaired people would choose to endure the inconvenience of hearing loss for a long time rather than easily try expensive hearing aids. As a result, hearing-aid sellers have to endlessly increase the selling price in order to obtain sufficient profits, which results in the vicious circle of high hearing aid prices.

In addition, everyone has different sensitivity to the decibel or frequency of sounds. Thus, the parameters of hearing aids need to be adjusted according to individual circumstances. In the current method, users can only directly go to the physical store for adjusting hearing aid parameters. However, after the user leaves the store and returns home, the user dissatisfies with the sound production of the hearing aids since the requirements for the sound parameters of the hearing aids are different due to different environments. If the fitting staff can directly operate at the remote end, the fitting staff can make adjustments based on the feedback received from the user's current environment in order to obtain the optimal prescription in the environment.

To overcome the abovementioned problems, the present invention provides a cloud-based hearing aid management system and a method thereof, so as to solve the aforementioned problems of the prior art.

SUMMARY OF THE INVENTION

The primary objective of the present invention is to provide a cloud-based hearing aid management system and a method thereof, which automatically choose suitable hearing aids used by users, effectively improve the efficiency of choosing and purchasing hearing aids, and simultaneously reduce the number of physical stores to effectively decrease costs.

Another objective of the present invention is to provide a cloud-based hearing aid management system and a method thereof, which enable the fitting staff in an environment different from an environment where the user is located to directly and automatically respond to the personal environmental needs, and adjust the hearing aid parameters at the remote end at any time, thereby reducing the time when users go to the physical store to adjust the hearing aid and effectively improving efficiency.

In order to achieve the foregoing objectives, a cloud-based hearing aid management system is provided, which includes a user device and a management server. The user device includes a user database, a user processor, a user output unit, a user input unit, and a user signal transceiver. The user database is configured to store at least one piece of audiometry information. The user processor is connected to the user database and configured to access information in the user database. The user output unit is connected to the user processor. The user processor is configured to extract the at least one piece of audiometry information in the user database and output it through the user output unit. The user input unit is connected to the user processor, and the user processor configured to generate an audiogram based on a user's input received by the user input unit indicating that if the at least one piece of audiometry information can be heard. The user signal transceiver is connected to the user processor. The user processor is configured to output the audiogram through the user signal transceiver. The management server, connected to the user device, includes a management signal transceiver, a management processor, and a management database. The management signal transceiver is connected to the user signal transceiver and configured to receive the audiogram. The management processor is connected to the management signal transceiver. The management processor is configured to receive and convert the audiogram into a hearing parameter, and extract a hearing-loss characteristic value from the audiogram. The management database is connected to the management processor and configured to store a hearing aid recommendation table. The management processor is configured to incorporate the hearing-loss characteristic value into the hearing aid recommendation table to generate corresponding hearing aid recommendation information.

In an embodiment, the audiogram includes decibels heard at different frequencies. The management processor is configured to average the decibels heard at each frequency to generate the hearing-loss characteristic value.

In an embodiment, the hearing aid recommendation table includes hearing-loss characteristic values in different numerical ranges, and the models of hearing aids corresponding to hearing-loss characteristic values in different numerical ranges.

In an embodiment, the management database is further configured to store a hearing prescription conversion formula and a hearing aid parameter adjustment table. The management processor is configured to incorporate the audiogram into the hearing prescription conversion table to generate hearing prescription information, and then incorporate the hearing prescription information into the hearing aid parameter adjustment table to generate hearing aid adjustment parameters.

In an embodiment, the hearing prescription conversion formula is implemented with NAL-NL2.

In an embodiment, the management processor is configured to control the management signal transceiver to send the hearing aid adjustment parameters to the user signal transceiver. The user processor is configured to control the user signal transceiver to transmit the hearing aid adjustment parameters to a corresponding hearing aid to adjust sound parameters generated by the corresponding hearing aid.

In an embodiment, the user signal transceiver is configured to transmit the hearing aid adjustment parameters to the corresponding hearing aid using a high-frequency encoded signal.

In an embodiment, the output unit is a sound-producing element.

In an embodiment, a cloud-based hearing aid management method includes: outputting, by a user device, audiometry information and generating an audiogram based on a user's input indicating that if the audiometry information can be heard; converting the audiogram into a hearing parameter and extracting a hearing-loss characteristic value from the audiogram; and incorporating the hearing-loss characteristic value into a hearing aid recommendation table to generate corresponding hearing aid recommendation information.

In an embodiment, after the step of extracting the hearing-loss characteristic value from the audiogram, the audiogram is incorporated into a hearing prescription conversion table to generate hearing prescription information, and then the hearing prescription information is incorporated into the hearing aid parameter adjustment table to generate hearing aid adjustment parameters.

In an embodiment, the audiogram includes decibels heard at different frequencies. The hearing-loss characteristic value is generated by averaging the decibels heard at each frequency.

In an embodiment, the hearing aid recommendation table includes hearing-loss characteristic values in different numerical ranges, and the models of hearing aids corresponding to hearing-loss characteristic values in different numerical ranges.

Below, the embodiments are described in detail in cooperation with the drawings to make easily understood the technical contents, characteristics and accomplishments of the present invention.

DETAILED DESCRIPTION OF THE INVENTION

The present invention can recommend a hearing aid suitable for the user by operating a remote computer. In addition, the fitting staff adjusts the sound producing parameters of the hearing aid according to the user's requirement, which provides a convenient new consumption method.

Figure 1:
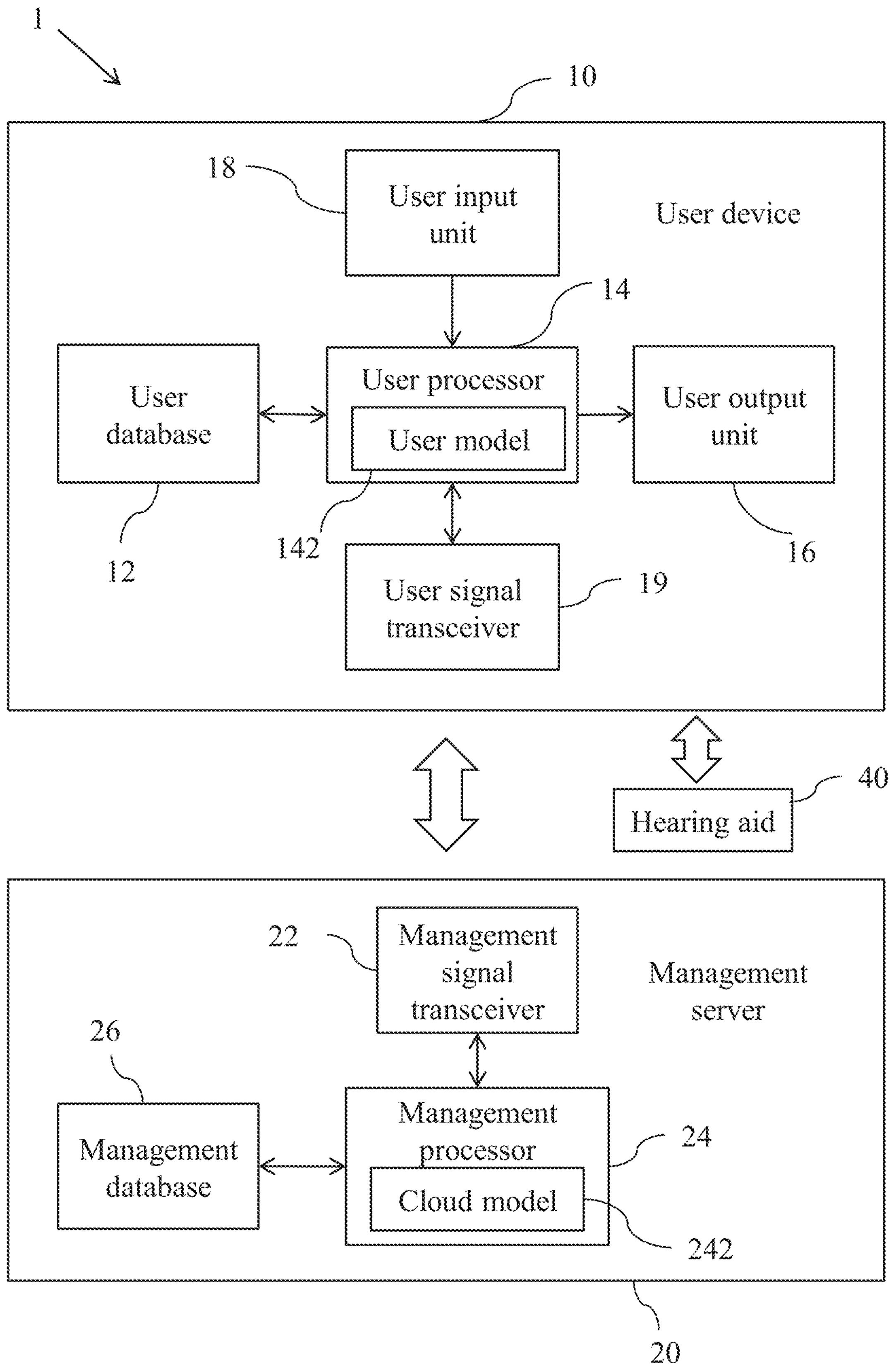
FIG. 1 is a schematic diagram illustrating a system according to an embodiment of the present invention.

How the present invention achieves the foregoing effects is described as follows. Referring to FIG. 1, the system architecture of the present invention is introduced. The present invention provides a cloud-based hearing aid management system 1, which includes a user device 10 and a management server 20. The user device 10 can be an intelligent mobile device with a communication function or a personal computers, etc. The management server 20 is a computer with communication and computing functions, so that the user device 10 can communicate with the management server 20.

The user device 10 includes a user database 12, a user processor 14, a user output unit 16, a user input unit 18, and a user signal transceiver 19. The user database 12 may be a memory, a hard disk, etc. The user database 12 is configured to store audiometry information, user's personal information (such as age, gender, language family, and whether it is the first time to wear it) and audiograms, the parameters of the hearing aid worn, the usage status of the hearing aid worn, the model of the hearing aid worn in the past, etc. In the embodiment, the audiometry information is a combination of sounds with various frequencies and decibels, which are provided to users to perform audiometry. By testing the decibels that users can hear in each frequency range, the user's hearing is tested. The user signal transceiver 19 uses some transmission methods such as Bluetooth, ultrasonic encrypted signals, and NFC, etc.

Figure 2:
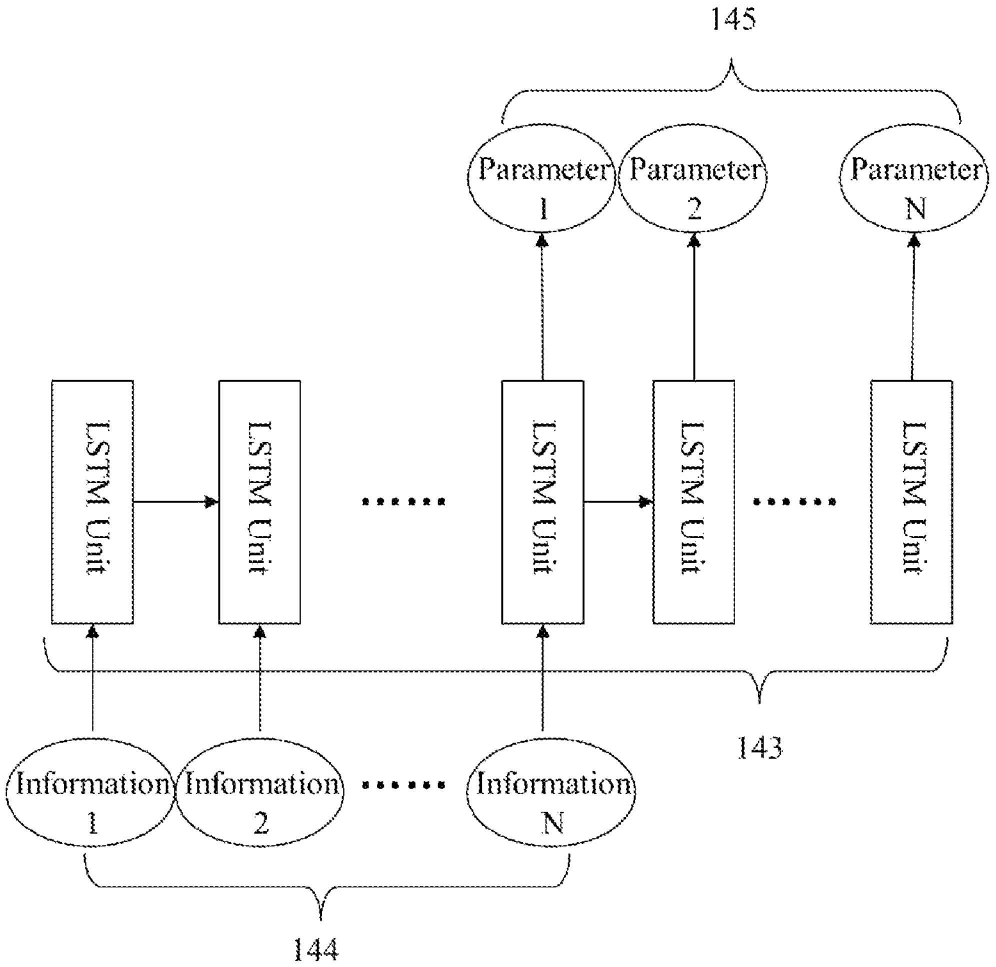
FIG. 2 is a schematic diagram illustrating a user model according to an embodiment of the present invention.

The user processor 14, connected to the user database 1, accesses information in the user database 12. The user processor 14 is a central processing unit (CPU) with a calculation function to perform calculations on various data. The user processor 14 includes a user model 142, which is implemented with a neural network model. The user processor 14 can use the data of each user to train a user model 142 suitable for each user. In other words, using federated learning, users can learn their own models and feed them back to the cloud to more accurately generate the overall prescription. In one embodiment, the user model 142 is implemented with a long short-term memory model (LSTM), which is many-to-many architecture. As illustrated in FIG. 2, the user model 142 includes a plurality of LSTM units (cells) 143. Each hearing parameter (referred to as information in FIG. 2) 144 is respectively inputted into one LSTM unit 143. After the LSTM units 143 calculate the hearing parameters layer by layer, parameters 145 are outputted. The parameter 145 is the weight calculated based on the customer's hearing loss status and customer's hearing preference. Finally, the weight is converted into a hearing prescription using the activation function.

In the embodiment, the user output unit 16 is a sound producing element. The user output unit 16 is connected to the user processor 14. After the user processor 14 extracts the audiometry information of the user database 12, the user's hearing information is played by the user output unit 16.

In the embodiment, the user input unit 18 is a keyboard, a button, or an element that can input information. The user input unit 18 is connected to the user processor 14. The user processor 14 configured to generate an audiogram based on a user's input received by the user input unit indicating that if at least one piece of audiometry information can be heard.

In the embodiment, the user signal transceiver 19 is a wireless communication transceiver. The user signal transceiver 19 is connected to the user processor 14 and controlled by the user processor 14. The user signal transceiver 19 can send out the audiogram.

The management server 20 is a cloud server, which includes a management signal transceiver 22, a management processor 24 and a management database 26. The management signal transceiver 22 is connected to the user signal transceiver 19. In the embodiment, the management signal transceiver 22 can be a wireless communication transceiver, which is configured to receive the audiogram transmitted by the user signal transceiver 19. The management processor 24 is connected to the management signal transceiver 22. The management processor 24 is generally a central processing unit (CPU) with a computing function to perform operations on data. The management processor 24 can receive the audiogram transmitted by the management signal transceiver 22 to convert the audiogram into a hearing parameter, and extract a hearing-loss characteristic value from the audiogram. Wherein the audiogram includes decibels heard at different frequencies, such decibels heard at a frequency of 1K Hz, decibels heard at a frequency of 2K Hz or decibels heard at a frequency of 4K Hz. When the management processor 24 extracts the hearing-loss characteristic value, the decibels heard at each frequency are averaged. That is to say, the decibels heard at 250 Hz, 500 Hz, 1K Hz, 2K Hz and 4K Hz are averaged to generate the hearing-loss characteristic value. The hearing-loss characteristic value is the pure-tone threshold average (PTA)=$(HL_{250}+HL_{500}+HL_{1K}+HL_{2K}+HL_{4K}+HL_{8K})/6$, where HL represents the hearing-loss value, and $HL_{frq}$ represents the hearing-loss value at the frequency frq.

When an audiometry test is performed on the user, the user only needs to operate the user input unit 18, such as pressing an audiometry button. In order to reduce the accuracy of the test results caused by the long test time of the user, the audiometry content will be played at frequencies of 250 Hz, 500 Hz, 1K Hz, 2K Hz and 4K Hz. For example, the audiometry content is measured when the volume of the audiometry content is higher than or equal to 60 dB. The hearing-loss value at each frequency represents the degree of hearing loss of the tester, so as to determine different hearing-loss statuses. If the audiometry process is interrupted, it will resume the interrupted part after reconnecting.

The management database 26 can be a memory or a hard disk for storing data. The management database 26 is connected to the management processor 24. The management database 26 stores a hearing aid recommendation table, a hearing prescription conversion formula, and a hearing aid parameter adjustment table. The hearing aid recommendation table includes hearing-loss characteristic values in different numerical ranges, and the models of hearing aids corresponding to hearing-loss characteristic values in different numerical ranges. Thus, the management processor 24 can incorporate the hearing-loss characteristic values into the hearing aid recommendation table to generate corresponding hearing aid recommendation information. When the management processor 24 establishes the hearing aid recommendation table, the models of hearing aids can be established first, and the hearing aid type, the number of hearing aids, the number of compression channels of hearing aids, the fitting depths of hearing aids, acoustic parameters including tubing specifications and venting specifications, compression speed, additional functions [e.g., Bluetooth® communication, rechargeable/battery type, noise reduction capability, etc.], suitable language family and other parameters are then set.

In order to reduce the accuracy of the test results caused by the user's too long test time, the audiometry content will be tested by progressively increasing the frequency of sounds. For example, the sound at 250 Hz is generated at the beginning. Then, the frequency of the sound slowly increases to 500 Hz from 250 Hz, slowly increases to 1000 Hz from 500 Hz, slowly increases to 2000 Hz from 1000 Hz, slowly increases to 4000 Hz from 2000 Hz, and slowly increases to 8000 Hz from 4000 Hz. The volume of the audiometry content is measured from 60 dB. During the audiometry process, the user only needs to press the button as long as the sound is heard by the user. The degree of hearing loss of the user is determined by the hearing-loss characteristic value at each frequency, as represented by the following formula (1):

$$PTA=(HL_{250}+HL_{500}+HL_{1K}+HL_{2K}+HL_{4K}+HL_{8K})/6 \tag{1}$$

Wherein, $HL_{frq}$ is the hearing-loss characteristic value at each of different frequencies. During the audiometry process, if an interruption event occurs, it will resume the interrupted part after reconnecting.

The hearing prescription conversion formula is implemented with NAL-NL2. Based on the hearing prescription conversion formula, the management processor 24 incorporates the audiogram into the hearing prescription conversion table to generate hearing prescription information. For example, the management processor 24 determines the audiogram to be a flat type audiogram, a high-frequency steep drop audiogram, a low-frequency hearing-loss audiogram, a middle-frequency hearing-loss audiogram, a noise-type hearing-loss audiogram, and an otosclerosis hearing-loss audiogram according to the audiometry results. When $Max(HL)-Min(HL)<20$ db, the management processor 24 determines the audiogram to be the flat type audiogram. Max(HL) represents the maximum hearing-loss value at all frequencies, and Min(HL) represents the minimum hearing-loss value at all frequencies. When $Max(HL_{4K}, HL_{8K})-Min(HL_{250}, HL_{500})\geq 20$ db & $HL_{4K}+HL_{8K}\geq HL_{1K}+HL_{2K}\geq HL_{250}+HL_{500}$, the management processor 24 determines that the audiogram to be the high-frequency steep drop audiogram. $Max(HL_{frq1}, HL_{frq2})$ represents the maximum hearing-loss values at frequencies frq1 and frq2, and $Min(HL_{frq1}, HL_{frq2})$ represents the minimum hearing-loss values at frequencies frq1 and frq2. When $Max(HL_{250}, HL_{500})-Min(HL_{4K}, HL_8K)\geq 20$ db & $HL_{250}+HL_{500}\geq HL_{1K}+HL_{2K}\geq HL_{4K}+HL_{8K}$, the management processor 24 determines that the audiogram to be the low-frequency hearing-loss audiogram. When $((HL_{1K}+HL_{2K})-(HL_{4K}+HL_{8K}))/2\geq 20$ db & $((HL_{1K}+HL_{2K})-(HL_{250}+HL_{500}))/2\geq 20$ db, the management processor 24 determines the audiogram to be the middle-frequency hearing-loss audiogram. When $HL_{K}-HL_{2K}\geq 20$ & $HL_{4K}-HL_{8K}\geq 20$ db, the management processor 24 determines the audiogram to be the noise-type hearing-loss audiogram. When $HL_{2K}-HL_{1K}\geq 20$ & $HL_{2K}-HL_{4K}\geq 20$ db, the management processor 24 determines the audiogram to be the otosclerosis hearing-loss audiogram.

The management processor 24 can further incorporate the hearing prescription information into the hearing aid parameter adjustment table to generate hearing aid adjustment parameters, so as to use the hearing aid adjustment parameters to adjust the sound-producing parameters of the hearing aid. For example, a database that stores the hearing aids of various brands may be firstly provided. Then, the remote adjustment parameters of the hearing aid are set, and an interface is provided to the manufacturer for customizing the adjustment parameters, which are provided to the remote server for adjusting API. In addition, it can be used with hearing aid testing instruments to automatically test and establish the acoustic parameters of hearing aids.

The management processor 24 then controls the management signal transceiver 22 to send the hearing aid adjustment parameters to the user signal transceiver 19. The user processor 14 controls the user signal transceiver 19 to transmit a high-frequency coded signal, which carries the hearing aid adjustment parameters, to a hearing aid 40, thereby adjusting the sound parameters produced by the hearing aid.

The management processor 24 further includes a cloud model 242 for generating hearing prescription information. The management processor 24 can receive a user model 142 fed back by each user device 10 for training the cloud model 242 so that the generated hearing prescription information is more accurate. The cloud model 242 is a neural network model. In one embodiment, the cloud model 242 is implemented with a long short-term memory (LSTM) model which is the same to the user model 142, as illustrated in FIG. 2.

In addition, the management database 26 can also store customers' satisfaction with the currently worn hearing aids, preferences for sound, and the like. For example, using the learning system, a set of learning contents for hearing aids can be designed for customers to understand the customer's satisfaction with the currently worn hearing aids and sound preferences. Then, the customer's satisfaction and the sound preferences are stored in the management database 26. The management processor 24 can provide preset course modules, or customize a course module for each customer. The course module mainly provides a variety of sounds for users to wear hearing aids to listen to, such as TV sounds, conversation sounds, wind sounds, bird sounds, newspaper rubbing sounds, and sounds that are often heard around. The customer's preference for the sound and the frequency band that needs to be added are determined by the satisfaction fed back after listening to these sounds.

Figure 3:
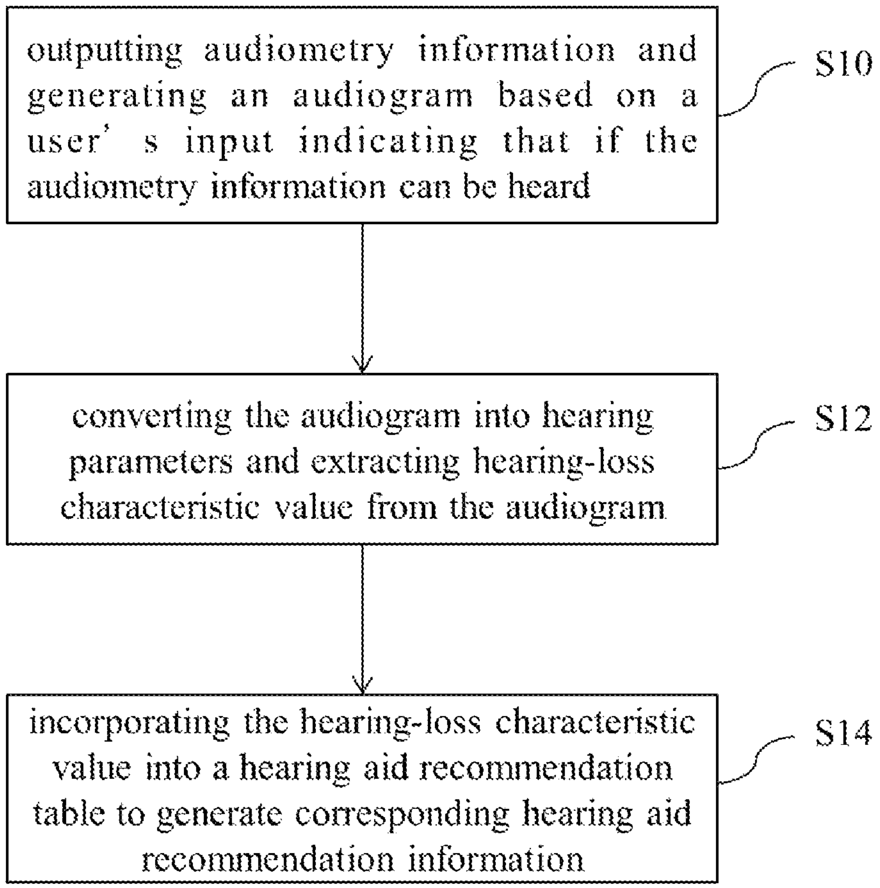
FIG. 3 is a flowchart of a method according to an embodiment of the present invention.
Figure 4:
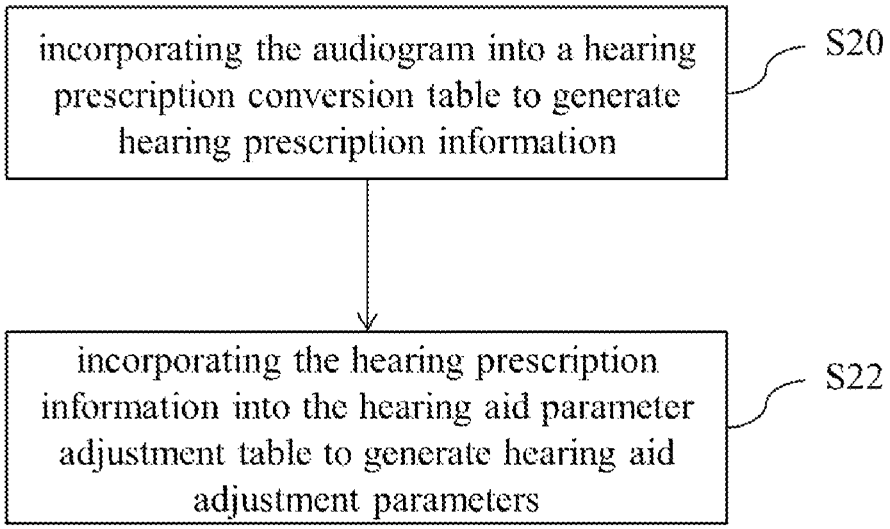
FIG. 4 is a flowchart of a method for generating hearing aid adjustment parameters according to an embodiment of the present invention.

After explaining the architecture of the present invention, the cloud-based hearing aid management method of the cloud-based hearing aid management system is explained as follows. Please refer to FIG. 1 and FIG. 3. The cloud-based hearing aid management method includes the following steps. In Step S10, the user processor 14 extracts the audiometry information from the user database 12, and employs the user output unit 16 to play the audiometry information of sounds. After the user listens to the audiometry information, the user inputs a feedback to indicates whether the audiometry information is hearable. Then, the user processor 14 correspondingly generate an audiogram. The hearing parameters of the audiogram can be expressed as 10 decibels heard at a frequency of 500 Hz and 5 decibels heard at a frequency of 2K Hz, etc.

After generating the corresponding audiogram, the process proceeds to Step S12. In Step S12, the user processor 14 controls the user signal transceiver 19 to transmit the audiogram to the management signal transceiver 22 of the management server 20. The management processor 24 receives the audiogram through the management signal transceiver 22, so that the management processor 24 converts the audiogram into hearing parameters. The audiogram is used to show the hearing parameters in the form of graphs and respectively show the audible decibels of each frequency. The management processor 24 converts the graphs into decibels. The management processor 24 then numerically averages the decibels heard at each frequency to generate the hearing-loss characteristic value.

Then, the process proceeds to Step S14. The management processor 24 then incorporates the hearing-loss characteristic value into the hearing aid recommendation table to generate corresponding hearing aid recommendation information. Furthermore, the management processor 24 can also incorporate compensation parameters, recommendation coefficients, user's personal information, etc. into the hearing aid recommendation table to generate more accurate hearing aid recommendation information. At this time, the management processor 24 can transmit the hearing aid recommendation information to the user signal transceiver 19 through the management signal transceiver 22. The user processor 14 can employ the user output unit 16 to display the hearing aid recommendation information. Thus, the user can obtain the suitable type of the hearing aid according to the hearing aid recommendation information.

For example, the compensation parameters of each hearing aid can be firstly established in the management database 26. Then, the management processor 24 calculates the recommendation coefficient of each hearing aid, and stores it in the management database 26. After the audiometry, the management processor 24 will automatically recommend a suitable hearing aid according to the relevant information of the tester (such as age, gender, region, language family, the models of previously used hearing aids, etc.) and the audiogram. In addition, the management processor 24 can also endlessly update the recommendation coefficient of each hearing aid according to the big data of the wearer and the usage status of the hearing aid.

In addition to the specification parameters, the age, gender, region, language family, hearing aid model, satisfaction degree, and wearing status of the past wearer will all affect the recommendation coefficient of the hearing aid. In addition, the degree of recommendation can be increased (not fully influenced) by purchasing advertising coefficients, so as to obtain advertising revenue. The recommendation coefficient can be calculated, for example, by the following formula: $RE=f_{HA}(HA, USER)*AD$, where RE is the recommendation coefficient, HA is the hearing aid compensation parameter, USER is the user's personal information, $f_{HA}$ is the basic recommendation coefficient generated by calculating the hearing aid compensation parameter and user parameters, and AD is an advertisement coefficient. The advertisement coefficient is an optional parameter.

Figure 5:
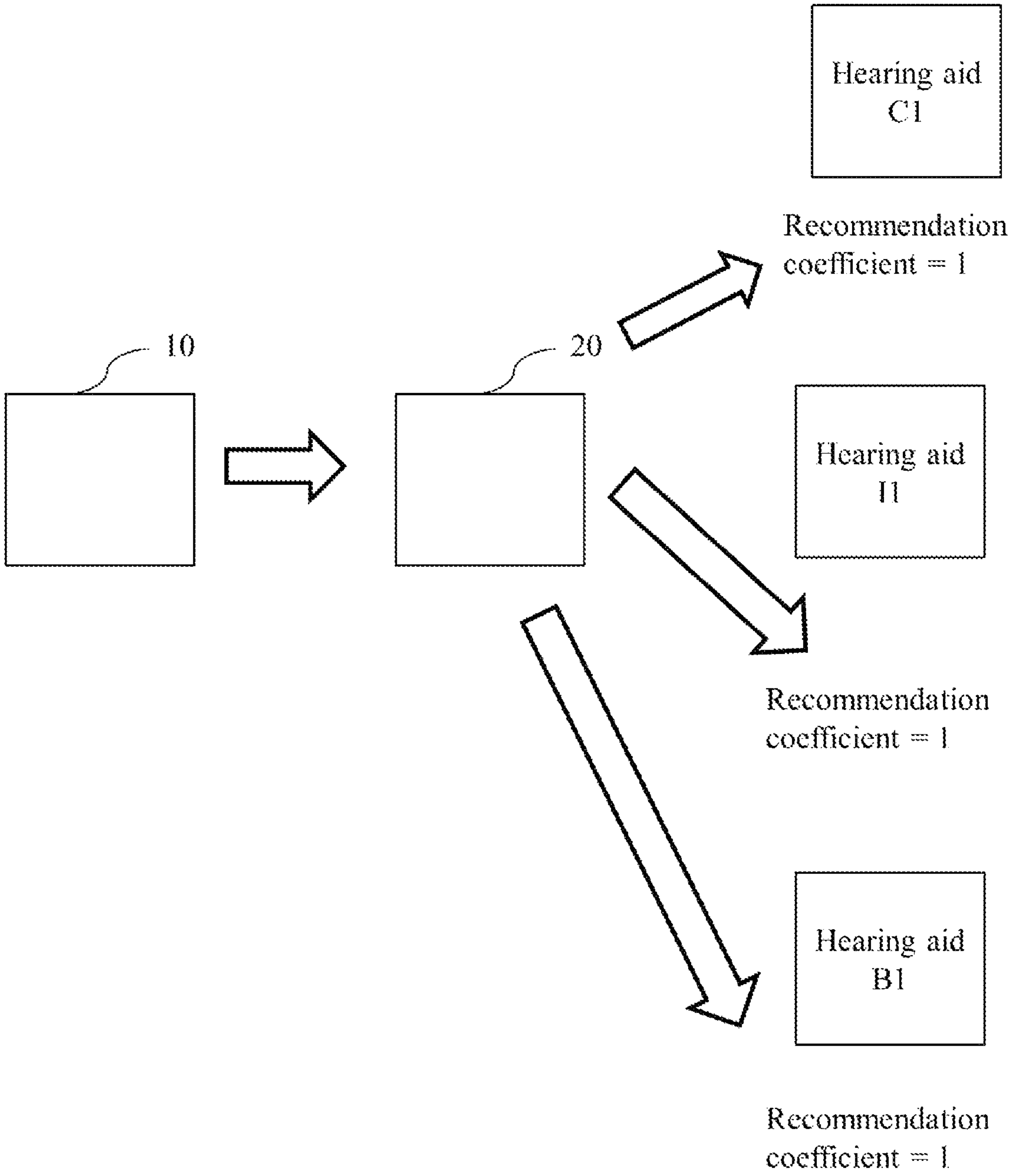
FIG. 5 is a schematic diagram illustrating a system for recommending hearing aids according to an embodiment of the present invention.
Figure 6:
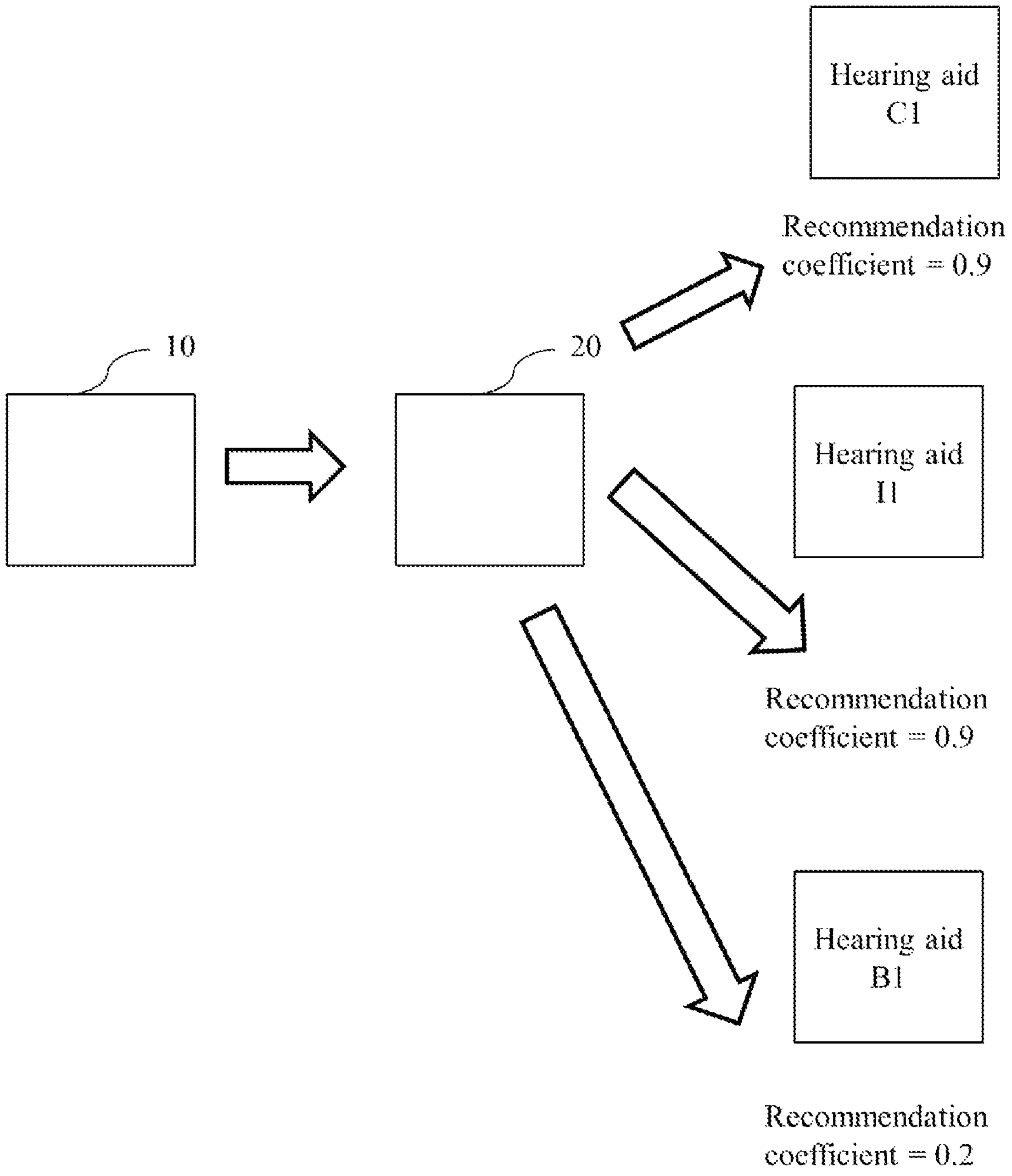
FIG. 6 is a schematic diagram illustrating a system for recommending hearing aids according to another embodiment of the present invention.
Figure 7:
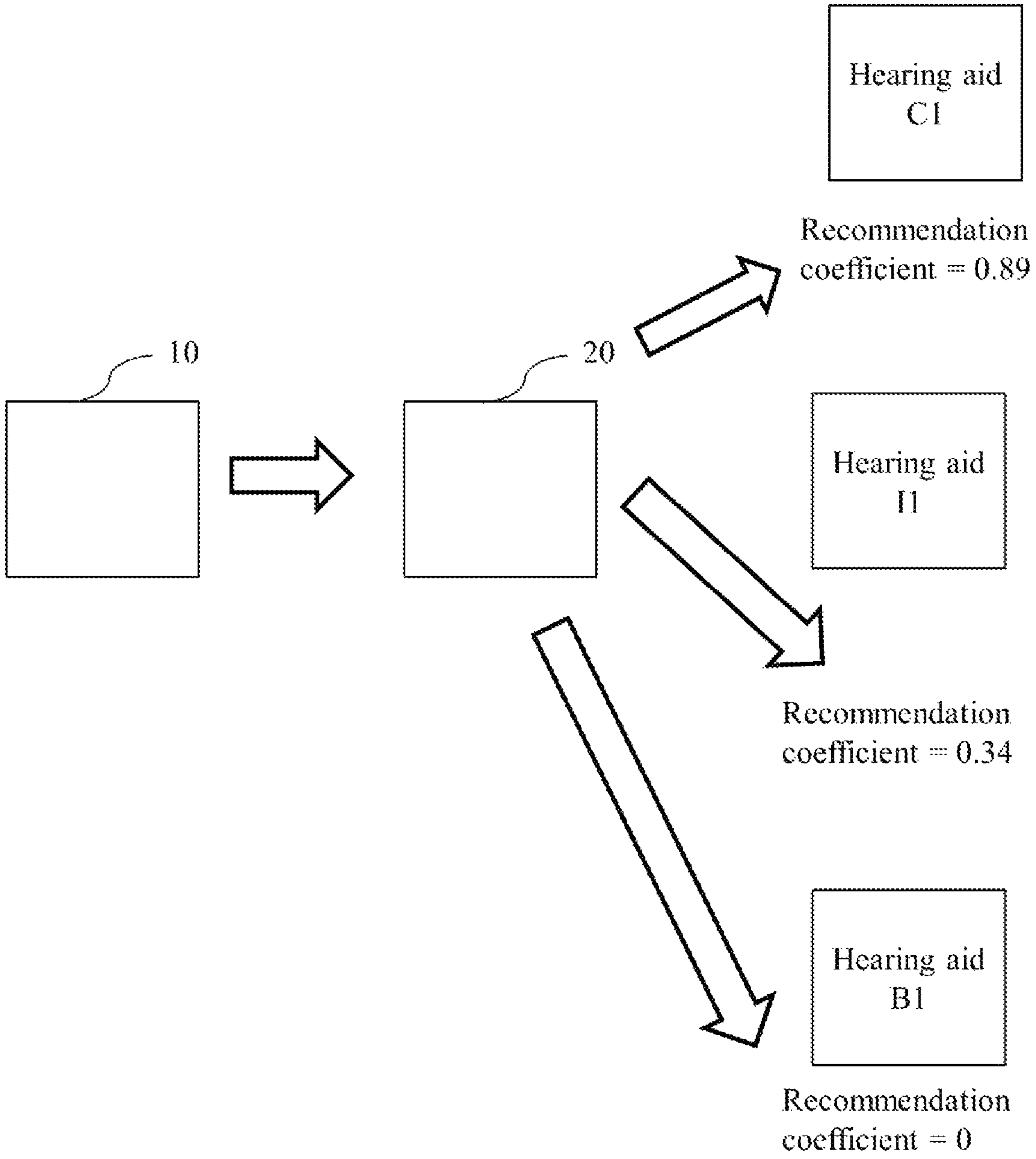
FIG. 7 is a schematic diagram illustrating a system for recommending hearing aids according to further embodiment of the present invention.

FIG. 5 is a schematic diagram illustrating a system for recommending hearing aids according to an embodiment of the present invention. Assume that the models of the hearing aids include hearing aids C1, I1, and B1. Please refer to FIG. 5. When the hearing aid compensation parameter HA outputted by the user device 10 and the user parameter USER are all unknown, the management server 20 calculates that the recommendation coefficients of the hearing aids C1, I1 and B1 are all 1. In other words, if the customer is completely unknown at the beginning, the recommendation coefficient will be the same. At this time, the recommendation list includes hearing aids C1, I1 and B1. FIG. 6 is a schematic diagram illustrating a system for recommending hearing aids according to an embodiment of the present invention. Please refer to FIG. 6. When the hearing aid compensation parameter HA outputted by the user device 10 is unknown and the user parameter USER belong to high frequency hearing loss, the management server 20 calculates that the recommendation coefficients of hearing aids C1, I1 and B1 are respectively 0.9, 0.9, and 0.2. The recommendation coefficient of the hearing aid B1 suitable for low-frequency hearing loss will be very low. At this time, the recommended list includes hearing aids C1 and I1. FIG. 7 is a schematic diagram illustrating a system for recommending hearing aids according to another embodiment of the present invention. Please refer to FIG. 7. When the hearing aid compensation parameter HA outputted by the user device 10 is equal to the specific hearing aid compensation parameter and the user parameter USER belongs to the high frequency heavy hearing loss plus the user hearing-loss value, the management server 20 calculates the recommendation coefficients of the hearing aids C1, I1 and B1 are 0.89, 0.34 and 0, respectively. At this time, the recommended list only includes hearing aid C1. From the foregoing embodiments, it can be seen that when the data of the hearing aid compensation parameter HA and the user parameter USER are clearer, the estimated accuracy of the recommendation coefficient is also higher.

In addition to recommending the types of suitable hearing aids, the present invention has other functions. When the user returns to the residence, the environment or physiological conditions may cause changes in hearing. In order to effectively respond to this situation, the present invention further provides a function for remotely adjusting the parameters of the hearing aid at any time. Please refer to FIGS. 1-4. In Step S20, the user can listen to the audiometry information again, re-input the hearing parameters, and generate a new audiogram. Step S20 is the same to Steps S10-S12 so it will not be reiterated. The management processor 24 can incorporate the audiogram into the hearing prescription conversion table to generate hearing prescription information. For example, the hearing prescription information suitable for the user is calculated based on the wearer's information stored in the user database 12 (such as age, gender, language family, and whether it is the first time to wear it), audiograms, the parameters of worn hearing aids, the records of course modules, the usage status of the wearer's hearing aids and the records of the hearing aids worn in the past. Assume that the input parameters include age 0.62, gender 1, language family 6, . . . , and ear type 4. The management processor 24 will normalize the input parameter. For example, if the age is set between 0 and 1, the normalized age of 62 will be set to 0.62. By the same token, the user model can be trained. The inputs are then combined into an input vector. For example, the prescription input vector×1=(0.62, 1, 6, . . . , 4). Then, the user model will learn the results that satisfy the user's requirements and preferences based on the prescription input vector, and finally output the vector $h_1=(o_1, o_2, o_3, \ldots, o_n)$ to obtain the optimal adjustment prescription, which includes prescription parameter $1=o_1$, prescription parameter $2=o_2$, prescription parameter $3=o_3$, and so on. That is to say, the output vector h1 sequentially corresponds to the new prescription parameters. Therefore, the user model can customize the most suitable adaptation prescription for the user. In the embodiment, the input parameters may also include earplug type, main use situation, secondary use situation, wearing time, the last audiogram, audiograms in recent 6 months (excluding the last one), the last dispensed prescriptions, dispensed prescriptions in recent 6 months (excluding the last one), sound pressure level (SPL), output gain, etc.

Figure 8:
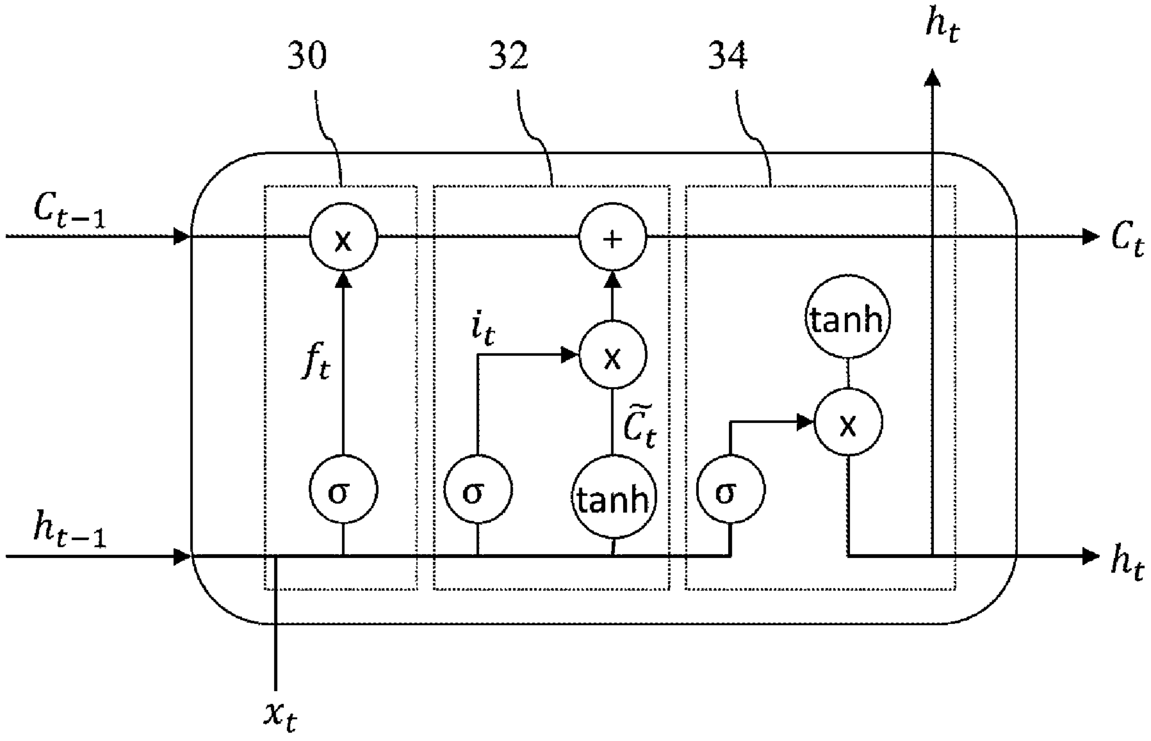
FIG. 8 is a schematic diagram illustrating a user model implemented with a single long short-term memory (LSTM) unit according to an embodiment of the present invention.
Figure 9:
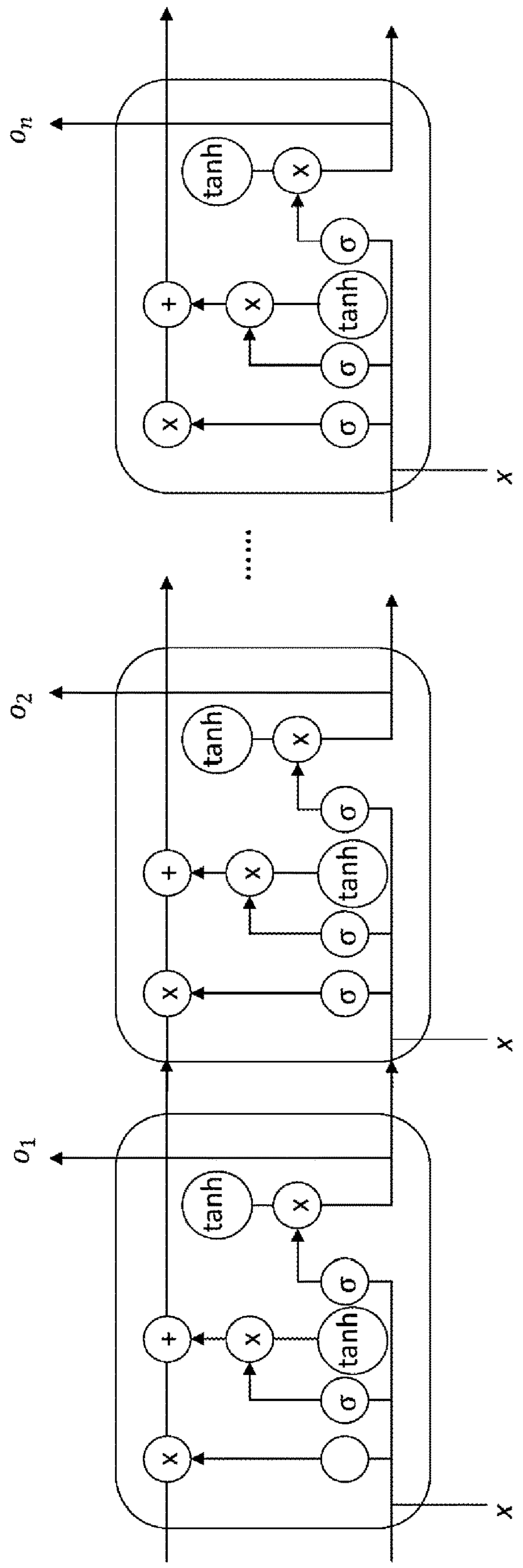
FIG. 9 is a schematic diagram illustrating a user model implemented with a plurality of long short-term memory (LSTM) units according to an embodiment of the present invention.

Please refer to FIG. 8 and FIG. 9 for the architecture of the user model. The neural network of the user model includes a forgetting valve 30, an input valve 32 and an output valve 34 connected in sequence. The user model calculates the prescription suitable for the wearer based on equations (2)~(7):

$$f_t = \sigma(W_f \cdot [h_{t-1}, x_t] + b_f) \tag{2}$$

$$i_t = \sigma(W_i \cdot [h_{t-1}, x_t] + b_i) \tag{3}$$

$$\tilde{C}_t = \tanh(W_C \cdot [h_{t-1}, x_t] + b_C) \tag{4}$$

$$C_t = f_t * C_{t-1} + i_t * \tilde{C}_r \tag{5}$$

$$O_t = \sigma(W_0 \cdot [h_{t-1}, x_t] + b_0) \tag{6}$$

$$h_t = O_t * \tanh(C_t) \tag{7}$$

Wherein, $f_1$ represents the result of the forgetting valve, σ represents the Sigmoid function, ht−1 represents the weight of the hidden layer of the previous Cell, ht represents the weight of the hidden layer of the new Cell, $x_t$ represents the input vector, $W_f[h_{t-1}, x_t]$ represents the weight of the forgetting valve including the input vector and the previous hidden layer, bf represents the offset value of the forgetting valve, it represents the result of the input valve, $W_i \cdot [h_{t-1}, x_1]$ represents the weight of the input valve including the input vector and the previous hidden layer, $b_i$ represents the offset value of the input valve, $\tilde{C}_t$ represents the new vector, tanh represents the tanh's activation function, $W_c \cdot [h_{t-1}, x_t]$ represents the weight of the new vector including the input vector and the previous hidden layer, $b_c$ represents the new vector, $C_t$ represents the state of the new Cell, $C_{t-1}$ represents the state of the old Cell, $O_t$ represents the result of the output valve, $W_O \cdot [h_{t-1}, x_t]$ represents the weight of the output valve including the input and the previous hidden layer, and $b_O$ represents the offset value of the output valve.

It is noted that the user model will use the various information of the wearer as an input, so that the user model can learn the wearer's preferences and satisfy the requirements of the wearer. Thus, the user model can be more customized. Each adjustment will be fed back to the user model. If the user model is not satisfied, the next good dispensed prescription fed back will be used as an input to adjust the user model, so that the user model can more satisfy with the wearer's requirements. For example, in the beginning, the basic information of a customer is inputted into a cloud model to recommend the best current prescription and generate a basic user model. When the wearer sends an adaptive request out, the user model will deduce from the previously integrated cloud experience that the wearer may need a low-frequency gain. If the wearer is not satisfied with the adaptive prescription, the result will be fed back to the user model, and the cloud model will also infer a new prescription. That is to say, because of feeding back the previous low-frequency gain and the new high-frequency gain, the user model will learn that the wearer may prefer high-frequency sound or that high-frequency sound is the main requirement of the wearer. Thus, the user model will prefer to recommend a prescription for high-frequency gain the next time.

In another embodiment, the automatic optimal adjustment prescription will be endlessly updated along with the wearer's wearing condition. The calculation steps of the automatic optimal adjustment prescription include the following equations: (8)~(12):

$$\Delta_t = \text{formula}_{ground} - \text{formula}_{pred} \quad (8)$$

$$\delta W_{gates} = F_w(W_{gates}, \Delta_t) \quad (9)$$

$$\delta b_{gates} = F_b(b_{gates}, \Delta_t) \quad (10)$$

$$\delta W_c = F_w(W_c, \Delta_t) \quad (11)$$

$$\delta b_c = F_b(b_c, \Delta_t) \quad (12)$$

Wherein, $\text{formula}_{ground}$ represents the optimal adjustment prescription finally satisfied by the user, $\text{formula}_{pred}$ represents the optimal adjustment prescription predicted by the model, $\Delta_t$ represents an error, $F_w$ represents a function for updating the weight of the model, $F_b$ represents a function for updating the offset value of the model, gates. represents the weights of the forgetting valve, the input valve, and the output valve, $\delta W_{gates}$ represents the new weights of the forgetting valve, the input valve, and the output valve after update, $b_{gates}$ represents the offset values of the forgetting valve, the input valve, and the output valve, $\delta b_{gates}$ represents the new offset values of the forgetting valve, the input valve, and the output valve after update, $W_c$ represents the weight of the cell, $\delta W_c$ represents the new weight of the cell after update, $b_c$ represents the offset value of the cell, and $\delta b_c$ represents the new offset value of the cell.

In Step S22, the management processor 24 then incorporates the hearing prescription information into the hearing aid parameter adjustment table to generate hearing aid adjustment parameters correspondingly. The management processor 24 can operate the management signal transceiver 22 to transmit the hearing aid adjustment parameters to the user signal transceiver 19 in a push-casting manner. Afterwards, the user processor 14 operates the user signal transceiver 19 to transmit a high-frequency coded signal that carries the hearing aid adjustment parameters to the hearing aid, so as to adjust the sound producing parameters of the hearing aid suitable for the user's state. Each hearing aid has its own adjustable content. For example, the adjustment content can include wide dynamic range compression (WDRC), equalizer (EQ), the maximum output volume (MPO), noise reduction (NR), feedback cancellation (FBC), etc.

In addition, the management server 20 can also provide online consultation. The online consultation can be performed after the user uses the user device 10 to complete the automatic audiometry, or when there is a problem related to hearing aids or hearing loss. After the automatic audiometry, the user can also use the user device 10 to choose whether to consult. If the management server 20 receives a consultation request after the automatic audiometry, the audiologist can connect to the management server 20 to obtain the data of the automatic audiometry as the material for consultation. In addition, the audiologist can measure other frequency points through the management server 20, so as to better understand the condition of the tester.

In conclusion, the present invention automatically choose suitable hearing aids used by users, effectively improve the efficiency of choosing and purchasing hearing aids, simultaneously reduce the number of physical stores to effectively decrease costs, enable the fitting staff in an environment different from an environment where the user is located to directly and automatically respond to the personal environmental needs, and adjust the hearing aid parameters at the remote end at any time, thereby reducing the time when users go to the physical store to adjust the hearing aid and effectively improving efficiency.

The embodiments described above are only to exemplify the present invention but not to limit the scope of the present invention. Therefore, any equivalent modification or variation according to the shapes, structures, features, or spirit disclosed by the present invention is to be also included within the scope of the present invention.

What is claimed is:

1. A cloud-based hearing aid management system comprising:

a user device comprising:

a user database configured to store at least one piece of audiometry information;

a user processor connected to the user database and configured to access information in the user database, the user processor includes a user model, which is a neural network model, and the user processor uses the information in the user database to train the user model suitable for a user by using federated learning, wherein the user model includes a forgetting valve, an input valve, and an output valve connected in sequence, and the user model calculates the prescription suitable for the user based on the following equations:

$$f_t=\sigma(W_f\cdot[h_{t-1},x_t]+b_f),$$

$$i_t=\sigma(W_i\cdot[h_{t-1},x_t]+b_i),$$

$$\tilde{C}_t=\tanh(W_C\cdot[h_{t-1},x_t]+b_C),$$

$$C_t=f_t*C_{t-1}+i_t*\tilde{C}_t,$$

$$O_t=\sigma(W_O\cdot[h_{t-1},x_t]+b_O), \text{ and}$$

$$h_t=O_t+*\tanh(C_t),$$

wherein $f_t$ represents a result of the forgetting valve, $\sigma$ represents the Sigmoid function, $h_{t-1}$ represents a weight of a hidden layer of a previous Cell, $h_t$ represents a weight of a hidden layer of a new Cell, $x_t$ represents an input vector, $W_f\cdot[h_{t-1},x_t]$ represents a weight of the forgetting valve including the input vector and the previous hidden layer, $b_f$ represents an offset value of the forgetting valve, $i_t$ represents a result of the input valve, $W_i\cdot[h_{t-1},x_t]$ represents a weight of the input valve including the input vector and the previous hidden layer, bi represents an offset value of the input valve, $\tilde{C}_t$ represents a new vector, tanh represents the tanh's activation function, $W_C\cdot[h_{t-1},x_t]$ represents a weight of the new vector including the input vector and the previous hidden layer, $b_C$ represents the new vector, $C_t$ represents a state of the new Cell, $C_{t-1}$ represents a state of the previous Cell, $O_t$ represents a result of the output valve, $W_O\cdot[h_{t-1},x_t]$ represents a weight of the output valve including the input and the previous hidden layer, and $b_O$ represents an offset value of the output valve;

a user output unit connected to the user processor, wherein the user processor is configured to extract the at least one piece of audiometry information in the user database and output it through the user output unit;

a user input unit connected to the user processor, wherein the user processor configured to generate an audiogram based on a user's input received by the user input unit indicating that if the at least one piece of audiometry information can be heard; and a user signal transceiver connected to the user processor, wherein the user processor is configured to output the audiogram through the user signal transceiver;

a management server, connected to the user device, comprising:

a management signal transceiver connected to the user signal transceiver and configured to receive the audiogram;

a management processor connected to the management signal transceiver, wherein the management processor is configured to receive and convert the audiogram into a hearing parameter, and extract a hearing-loss characteristic value from the audiogram, the management processor further includes a cloud model, which is a is a neural network model, the management processor receives the user model fed back by the user device for training the cloud model; and a management database connected to the management processor and configured to store a hearing aid recommendation table, wherein the management processor is configured to incorporate the hearing-loss characteristic value into the hearing aid recommendation table to generate corresponding hearing aid recommendation information for the cloud model of the management processor to generate hearing aid adjustment parameters, and the hearing aid recommendation table comprises hearing-loss characteristic values in different numerical ranges, and models of hearing aids corresponding to hearing-loss characteristic values in different numerical ranges, and wherein the management database is further configured to store a hearing prescription conversion formula and a hearing aid parameter adjustment table, and the management processor is configured to incorporate the audiogram into the hearing prescription conversion table to generate hearing prescription information, and then incorporate the hearing prescription information into the hearing aid parameter adjustment table to generate hearing aid adjustment parameters, and the management processor calculates the prescription suitable for the user based on the following equations:

$$\Delta_t = \text{formula}_{ground} - \text{formula}_{pred}$$

$$\delta W_{gates} = F_W(W_{gates}, \Delta_t)$$

$$\delta b_{gates} = F_b(b_{gates}, \Delta_t)$$

$$\delta W_c = F_w(W_c, \Delta_t)$$

$$\delta b_c = F_b(b_c, \Delta_t)$$

wherein, $\text{formula}_{ground}$ represents the optimal adjustment prescription finally satisfied by the user, $\text{formula}_{pred}$ represents the optimal adjustment prescription predicted by the model, $\Delta_t$ represents an error, $F_W$ represents a function for updating the weight of the model, $F_b$ represents a function for updating the offset value of the model, $W_{gates}$ represents the weights of the forgetting valve, the input valve, and the output valve, $\delta W_{gates}$ represents the new weights of the forgetting valve, the input valve, and the output valve after update, $b_{gates}$ represents the offset values of the forgetting valve, the input valve, and the output valve, $\delta b_{gates}$ represents the new offset values of the forgetting valve, the input valve, and the output valve after update, $W_c$ represents the weight of the cell, $\delta W_c$ represents the new weight of the cell after update, $b_c$ represents the offset value of the cell, and $\delta b_c$ represents the new offset value of the cell; and a hearing aid, connected to the user device, wherein the management processor sends the hearing aid adjustment parameters to the user signal transceiver and controls the user signal transceiver to transmit the hearing aid adjustment parameter to the hearing aid to adjust sound parameters generated by the hearing aid.

2. The cloud-based hearing aid management system according to claim 1, wherein the audiogram comprises decibels heard at different frequencies, and the management processor is configured to average the decibels heard at each frequency to generate the hearing-loss characteristic value.

3. The cloud-based hearing aid management system according to claim 1, wherein the hearing prescription conversion formula is implemented with NAL-NL2.

4. The cloud-based hearing aid management system according to claim 1, wherein the user signal transceiver is configured to transmit the hearing aid adjustment parameters to the corresponding hearing aid using a high-frequency encoded signal.

5. The cloud-based hearing aid management system according to claim 1, wherein the output unit is a sound-producing element.

6. A cloud-based hearing aid management method, comprising:

outputting, by a user device, audiometry information and generating an audiogram based on a user's input indicating that if the audiometry information can be heard;

training a user model suitable for the user using the audiometry information by the user device using federated learning, wherein the user model includes a forgetting valve, an input valve, and an output valve connected in sequence, and the user model calculates the prescription suitable for the user based on the following equations:

$$f_t = \sigma(W_f \cdot [h_{t-1}, x_t] + b_f),$$

$$i_t = \sigma(W_i \cdot [h_{t-1}, x_t] + b_i),$$

$$\tilde{C}_t = \tanh(W_C \cdot [h_{t-1}, x_t] + b_C),$$

$$C_t = f_t * C_{t-1} + i_t * \tilde{C}_t,$$

$$O_t = \sigma(W_O \cdot [h_{t-1}, x_t] + b_0), \text{ and}$$

$$h_t = O_t + * \tanh(C_t),$$

wherein $f_t$ represents a result of the forgetting valve, $\sigma$ represents the Sigmoid function, $h_{t-1}$ represents a weight of a hidden layer of a previous Cell, $h_t$ represents a weight of a hidden layer of a new Cell, $x_t$ represents an input vector, $W_f \cdot [h_{t-1}, x_t]$ represents a weight of the forgetting valve including the input vector and the previous hidden layer, $b_i$ represents an offset value of the forgetting valve, it represents a result of the input valve, $W_i \cdot [h_{t-1}, x_t]$ represents a weight of the input valve including the input vector and the previous hidden layer, bi represents an offset value of the input valve, $\tilde{C}_t$ represents a new vector, tanh represents the tanh's activation function, $W_C \cdot [h_{t-1}, x_t]$ represents a weight of the new vector including the input vector and the previous hidden layer, $b_C$ represents the new vector, $C_t$ represents a state of the new Cell, $C_{t-1}$ represents a state of the previous Cell, $O_t$ represents a result of the output valve, $W_O \cdot [h_{t-1}, x_t]$ represents a weight of the output valve including the input and the previous hidden layer, and $b_O$ represents an offset value of the output valve, transmitting the audiogram and the user model to a management server by the user device, converting the audiogram into a hearing parameter and extracting a hearing-loss characteristic value from the audiogram by the management server, wherein the management server includes a cloud model, which is a neural network model, and the cloud model is trained with the user model;

incorporating the audiogram into a hearing prescription conversion table by the management server to generate hearing prescription information, and then the hearing prescription information is incorporated into the hearing aid parameter adjustment table to generate hearing aid adjustment parameters;

transmitting the hearing aid adjustment parameters to a corresponding hearing aid to adjust sound parameters generated by the corresponding hearing aid;

calculating the prescription suitable for the user by the management server based on the following equations:

$$\Delta_t = \text{formula}_{ground} - \text{formula}_{pred}$$

$$\delta W_{gates} = F_W(W_{gates}, \Delta_t)$$

$$\delta b_{gates} = F_b(b_{gates}, \Delta_t)$$

$$\delta W_c = F_w(W_c, \Delta_t)$$

$$\delta b_c = F_b(b_c, \Delta_t)$$

wherein, $\text{formula}_{ground}$ represents the optimal adjustment prescription finally satisfied by the user, $\text{formula}_{pred}$ represents the optimal adjustment prescription predicted by the model, A represents an error, $F_W$ represents a function for updating the weight of the model, $F_b$ represents a function for updating the offset value of the model, $W_{gates}$ represents the weights of the forgetting valve, the input valve, and the output valve, $\delta W_{gates}$ represents the new weights of the forgetting valve, the input valve, and the output valve after update, $b_{gates}$ represents the offset values of the forgetting valve, the input valve, and the output valve, $\delta b_{gates}$ represents the new offset values of the forgetting valve, the input valve, and the output valve after update, $W_c$ represents the weight of the cell, $\delta W_c$ represents the new weight of the cell after update, $b_c$ represents the offset value of the cell, and $\delta b_c$ represents the new offset value of the cell; and incorporating the hearing-loss characteristic value into a hearing aid recommendation table by the management server for the cloud model to generate corresponding hearing aid recommendation information, wherein the hearing aid recommendation table comprises hearing-loss characteristic values in different numerical ranges, and models of hearing aids corresponding to hearing-loss characteristic values in different numerical ranges.

7. The cloud-based hearing aid management method according to claim 6, wherein the hearing prescription conversion formula is implemented with NAL-NL2.

8. The cloud-based hearing aid management method according to claim 6, wherein the audiogram comprises decibels heard at different frequencies, and the hearing-loss characteristic value is generated by averaging the decibels heard at each frequency.

* * * * *